United States Patent [19]

Wu

[11] Patent Number: 4,885,240

[45] Date of Patent: * Dec. 5, 1989

[54] USE OF ORGANIC BUFFERS TO REDUCE DEHYDROASCORBIC ACID INTERFERENCE IN ANALYTICAL METHODS

[75] Inventor: Annie L. Wu, Penfield, N.Y.

[73] Assignee: Eastman Kodak Company, Rochester, N.Y.

[*] Notice: The portion of the term of this patent subsequent to May 24, 2005 has been disclaimed.

[21] Appl. No.: 903,532

[22] Filed: Sep. 4, 1986

[51] Int. Cl.$^4$ ............................................. C12Q 1/04
[52] U.S. Cl. .................................... 435/34; 435/4; 435/31; 435/38; 435/39; 435/805; 435/810; 436/1; 436/63; 436/93; 436/164; 436/169; 436/170; 436/171; 436/172; 436/805; 436/904; 422/56; 422/61
[58] Field of Search ............... 435/4, 34, 31, 38, 39, 435/805, 810; 436/1, 63, 93, 164, 169, 170, 171, 172, 805, 904; 422/56, 61; 558/412, 417; 560/27, 28, 115

[56] References Cited

U.S. PATENT DOCUMENTS

| | | | |
|---|---|---|---|
| 3,411,887 | 11/1968 | Ku | 23/230 |
| 3,867,259 | 2/1975 | Forgione | 435/26 |
| 3,929,580 | 12/1975 | Forgione | 435/26 |
| 4,026,767 | 5/1977 | Shih | 435/34 |
| 4,168,146 | 9/1979 | Grubb | 436/527 |
| 4,168,205 | 9/1979 | Danninger et al. | 435/10 |
| 4,247,297 | 1/1981 | Berti et al. | 23/230 B |
| 4,525,453 | 6/1985 | Guardino | 435/34 |
| 4,558,007 | 12/1985 | Anderson | 435/26 |
| 4,610,961 | 9/1986 | Guardino | 435/34 |
| 4,746,607 | 5/1988 | Mira et al. | 435/25 |

OTHER PUBLICATIONS

Good: Biochemistry 5(2), pp. 467–477 (1966).
Tanaka et al., *Eiyo to Shokuryo, 21(2), pp. 85–88, (1968), English Language Translation.*

Primary Examiner—Robert Benson
Attorney, Agent, or Firm—J. Lanny Tucker

[57] ABSTRACT

The interference of dehydroascorbic acid, an oxidation product of ascorbic acid, in analytical methods is reduced with the use of certain nitrogen-containing organic buffers. Dehydroascorbic acid tends to cause premature reduction of reducible compounds which are used to provide detectable species in the presence of an analyte. These organic buffers, as opposed to inorganic buffers, prevent premature reduction of the reducible compounds. An analytical method can be carried out in solution or in a dry analytical element.

18 Claims, No Drawings

USE OF ORGANIC BUFFERS TO REDUCE DEHYDROASCORBIC ACID INTERFERENCE IN ANALYTICAL METHODS

FIELD OF THE INVENTION

The present invention relates to clinical chemistry. It particularly relates to a composition, element and method for the determination of an analyte in the presence of dehydroascorbic acid, a potential interferent.

BACKGROUND OF THE INVENTION

In the clinical and pharmaceutical arts, brewing, food and chemical manufacturing industries, redox reactions are of great interest for the determination of various chemical and biological substances, called analytes herein. In many cases, these analytes are enzymes, substrates for enzymes, or microorganisms which contain enzymes which can participate in redox reactions. Generally, these reactions are evaluated photometrically by determining the formation or disappearance of a chromogen or fluorogen.

However, in many fluids which are being analyzed, such as biological fluids, there are substances which are strong reducing agents and can act as interferents by prematurely causing dye formation. Ascorbic acid is one such substance. Ascorbic acid, or Vitamin C, is a common interferent found in the body fluids of many people. According to U.S. Pat. No. 4,168,205 (issued Sept. 18, 1979 to Danninger et al), unwanted ascorbic acid can be removed by converting it to dehydroascorbic acid by the action of ascorbic acid oxidase. In many instances, this technique sufficiently removes the interference in the assay.

However, in some assays, dehydroascorbic acid can still be a significant interferent. For example, in assays where reducible compounds are used to provide a detectable species, the presence of even a small amount of a reductant such as dehydroascorbic acid can cause a significant error.

Therefore, it would be desirable to have a means for eliminating the interfering effect of dehydroascorbic acid in any assay utilizing a reducible compound.

SUMMARY OF THE INVENTION

The problems noted above are avoided with an aqueous analytical composition for the determination of an analyte comprising:

(a) a compound capable of being reduced to provide a detectable species by an analyte and dehydroascorbic acid, and (b) a nitrogen-containing organic buffer which buffers the composition at physiological pH.

This invention also provides an analytical element for the determination of an analyte comprising an absorbent carrier material and containing:

(a) a compound capable of being reduced to provide a detectable species by an analyte and dehydroascorbic acid, and (b) a nitrogen-containing organic buffer which buffers the composition at physiological pH.

A method for the determination of an analyte which is substantially unaffected by the presence of dehydroascorbic acid comprises the steps of:

A. contacting a sample of a liquid suspected of containing an analyte and dehydroascorbic acid with (a) a compound capable of being reduced to provide a detectable species by the analyte and dehydroascorbic acid, and (b) a nitrogen-containing organic buffer which buffers the composition at physiological pH, and B. determining the detectable species resulting from the presence of the analyte.

The present invention provides a highly sensitive redox assay for various analytes, and particularly for living organisms. The potentially interfering effect of dehydroascorbic acid is eliminated or substantially reduced in the assay of this invention by the use of nitrogen-containing organic buffers.

DETAILED DESCRIPTION OF THE INVENTION

The buffers useful in the practice of this invention are nitrogen-containing organic buffers. Such buffers are generally composed of carbon and hydrogen atoms and one or more nitrogen atoms, and optionally oxygen, sulfur or other nonmetallic atoms. They are generally nitrogen-containing aliphatic, aromatic or heterocyclic compounds. Examples of useful buffers are included among those reported by Good et al in *Biochemistry*, 5, 467 (1966), and *Anal. Biochem.*, 104, 300 (1980). The organic buffers useful in this invention are to be distinguished from inorganic buffers such as borate, phosphate, dimethylarsinic acid, sodium cacodylate, and the like which are not useful herein because they tend to reduce assay sensitivity.

Particularly useful nitrogen-containing buffers are the following:

N-tris(Hydroxymethyl)methyl-2-amineothanesulfonic acid, (TES),
Triethylamine,
N-2-Hydroxyethylpiperazine-N'-2-ethanesulfonic acid, (HEPES),
3-(N-Morpholino)propanesulfonic acid, (MOPS),
Tris(hydroxymethyl)aminomethane, (TRIS),
Bis(2-hydroxyethyl)iminotris(hydroxymethyl)-methane, (BISTRIS),
N,N-bis(2-Hydroxyethyl)-2-aminoethanesulfonic acid, (BES),
N,N-bis(2-Hydroxyethyl)glycine, (Bicine),
N-tris(Hydroxymethyl)methylglycine, (Tricine),
Imidazole,
N,N-Dimethylglutaric acid,
N-(2-Acetamido)-2-amineoethanesulfonic acid, (ACES),
N-Ethylmorpholine,
Diethanolamine,
2-Amino-2-methyl-1,3-propanol,
Trimethylpyridine, and
Barbituric acid.

Preferred organic buffers in the practice of this invention are N-tris(hydroxymethyl)methyl-2-aminoethanesulfonic acid and tris(hydroxymethyl)aminomethane.

The assay of this invention is carried out at physiological pH (that is 9 or less), and preferably at a pH of from about 6.5 to about 8.5.

It will be understood by those skilled in the art that for each buffer useful in the present invention there will be an optimal concentration range for substantially reducing or eliminating the interfering effect of dehydroascorbic acid. Generally, the buffers will be useful at a concentration of at least about 0.005, and preferably from about 0.05 to about 0.5, millimolar. In dry assays, the buffers can be used at a dry coating coverage of at least about 0.1, and preferably from about 0.5 to about 2, g/m$^2$.

The reducible compound useful in the practice of this invention can be any material that, in its oxidized form, is capable of being reduced by the analyte via one or more reactions to produce a detectable species. Such species can be detected by any suitable means including potentiometric or radiometric means. Preferably, as defined below, the species is detected with radiometric means.

A partial listing of various detectable species that are directly detectable by radiometric means includes colorimetrically detectable materials (such as chromogens), radiation emission materials (such as fluorogens), chemiluminescent materials, radioactive isotopes, phosphorescent materials, etc.

The use of chromogens or fluorogens is preferred in the practice of this invention. Such materials can be in the form of dyes or dye-providing compounds.

Examples of dyes or dye-providing compounds that can be used as reducible compounds include methylene blue, dichloroindophenol, resazurin, and various tetrazolium compounds, such as 3-(4,5-dimethyl-2-thiozolyl)-2,5-diphenyl-2H-tetrazolium bromide, 2,3,5-triphenyl-2H-tetrazolium chloride, tetranitro blue, tetrazolium chloride and nitrotetrazolium violet, and others described, for example in U.S. Pat. No. 4,525,453 (issued June 25, 1985 to Guardino et al).

The reducible compounds that are particularly useful in this invention are broadly defined as organic compounds containing a shiftable detectable species which can be reduced at physiological pH (that is 9 or less) to release the shiftable detectable species. The term "shiftable" is defined as: (1) a chromogen moiety, which has a first spectral absorption band while attached to the reducible compound and a second spectral absorption band when released, or a fluorogen moiety, which has first spectral excitation and emission bands while attached to the reducible compound and second spectral excitation and emission bands when released, (2) a chemically or biologically useful moiety which is inactive, blocked or otherwise inaccessible when attached to the reducible compound but active, unblocked or accessible when released, or (3) a chemically or biologically useful moiety which is active or accessible when attached to the reducible compound but inactive or otherwise inaccessible when released.

Thus, the detectable species is chemically modified when attached to the reducible compound, e.g. for (1) above the spectral band or bands of the reducible compound are shifted from the band or bands that the species has when released. Generally but not necessarily, the band or bands are relocated to substantially shorter wavelengths when the species is a part of the reducible compound. In all cases, the bands do not overlap to a significant extent. The shift from one spectral band to another can be due to the mere release of the moiety from the reducible compound, or alternatively, it can be caused by such release coupled with either interaction of the released moiety with metal ions or a mordant, or coupled with a change in the assay environment (for example, a change in pH). With any such change in the environment, the pH must remain at 9 or less.

Also, as noted above, the shiftable detectable species can also be a chemically or biologically useful moiety which, when attached to the reducible compound, is inactive or blocked or otherwise inaccessible, but when released at physiological pH becomes biologically or chemically active or accessible for further interaction. The released, active species can be detectable itself or is capable of one or more subsequent chemical, physical or biological reactions to provide a detectable species. The method of this invention provides a means for releasing such moieties, for example, electron transfer agents, enzymes, enzyme substrates, enzymes inhibitors, cofactors, catalysts or reactants upon reduction of the reducible compound, preferably at physiological pH, for a variety of chemical or biological purposes.

Further, a shiftable detectable species can be a chemically or biologically useful moiety which, when attached to the reducible compound, is active, or otherwise accessible for one or more subsequent chemical, physical or biological reactions, but when released at physiological pH becomes inactive or otherwise inaccessible for such reactions.

More particularly, the reducible compounds have the structure CAR-(-R$^1$)$_n$ wherein CAR— represents a substituted or unsubstituted aromatic or quinone nucleus, R$^1$ is a moiety comprising a detectable species defined herein, and n is 1 or 2. Examples of such nuclei are presented below. Further, when R$^1$ is replaced by H, CAR-(-H)$_n$ has a reduction potential (E$_\frac{1}{2}$) of either at least about +100 mV when measured in water, or of at least about −650 mV when measured in acetonitrile. This E$_{178}$ value facilitates the reduction and subsequent release of the detectable species from the compound at physiological pH. Such measurements are made according to standard electrochemical techniques using either polarography or cyclic voltametry (see, e.g. Sawyer and Roberts, Jr., *Experimental Electrochemistry for Chemists*, John Wiley & Sons, New York, 1974). Preferably, the E$_\frac{1}{2}$ is from about +100 mV to about +400 mV as measured in water, or from about −650 to about −300 mV as measured in acetonitrile. Both ranges are given because some of the reducible compounds are best measured in water whereas others are best measured in acetonitrile. Further details of measuring the E$_\frac{1}{2}$ are described below prior to Table I. The desired E$_\frac{1}{2}$ is achieved by appropriate electron withdrawing groups on the CAR— nucleus, by a fused, strained ring attached to the nucleus, or a combination of both.

In one embodiment, the reducible compounds can be reduced to provide a detectable species through quinone methide formation, similar to the description by Van de Sande in *Angew. Chem. Int. Ed. Engl.* 22, pp. 191–209 (1983) and U.S. Pat. No. 4,232,107 (issued Nov. 4, 1980 to Janssens), but which have the desired E$_\frac{1}{2}$ properties.

In another embodiment, useful reducible compounds include sulfilimides and sulfenylsulfonamides similar to those described on page 206 of the Van de Sande reference noted above, but which have the desired E$_\frac{1}{2}$ properties.

In still another embodiment, the reducible compounds are water-compatible, reducible compounds as described in Mura et al, U.S. Ser. No. 868,855 filed May 30, 1986. Water-compatible compounds are those defined as being more readily dissolvable (or soluble) in polar organic solvents (for example, alcohols, acetonitrile, N,N-dimethylformamide or dimethylsulfoxide), water or aqueous solutions containing a minor amount of one or more polar organic solvents, than in nonpolar organic solvents. Which solvents are polar and nonpolar is readily determinable by one of ordinary skill in the art. This water-compatibility is imparted by one or more water-compatibilizing substituents on the compound. Such substituents are broadly defined as moieties which have a hydrophobic parameter ($P_1$) less than about −2.0. Such a parameter is a standard value for a given moiety as described, for example, in *Quantitative Drug Design* by Y. Martin, Marcel Dekker, Inc., New York, 1978. These moieties are either readily ionizable in water (for example, carboxy or sulfo) or nonionizable in water (for example, iodoxy or glucosyl). A preferred water-compatibilizing substituent is carboxy. Other useful substituents include hydroxy, quaternary ammonium and sulfonamido. The substituents can be placed on the CAR— portion of the molecule or on the $R^1$ portion, or on both.

In a preferred embodiment, the reducible compounds are identified herein as RIND compounds, that is, reducible compounds capable of undergoing intramolecular nucleophilic displacement as physiological pH to release one or more detectable species when a nucleophilic group is generated by at least a one electron reduction of the compound. In other words, such displacement occurs when the RIND compound is reduced by a suitable reductant which provides the necessary electrons (described in more detail below).

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

Particularly useful RIND compounds are those represented by the structure CAR—$R^1$ wherein CAR— is

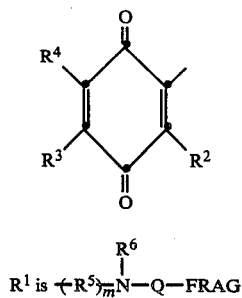

$R^1$ is $+R^5)_{\overline{m}}N-Q-FRAG$ wherein m is 0 or 1, and preferably 1. $R^5$ is substituted or unsubstituted alkylene, preferably of 1 or 2 carbon atoms in the backbone (for example, methylene, ethylene or alkoxymethylene). Most preferably, $R^5$ is methylene. Q is carbonyl or thiocarbonyl and preferably carbonyl.

$R^6$ is substituted or unsubstituted alkyl preferably of 1 to 40 carbon atoms (for example, methyl, ethyl, n-propyl, t-butyl, benzyl, lauryl, n-butyl, or n-hexyl), substituted or unsubstituted cycloalkyl preferably of 4 to 40 carbon atoms (for example, cyclobutyl, cyclohexyl or 4-methylcyclohexyl), substituted or unsubstituted heterocycle preferably of 5 to 40 atoms (carbon and heteroatoms, for example, pyridyl), or substituted or unsubstituted aryl preferably of 6 to 40 carbon atoms (for example, phenyl, xylyl, naphthyl, p-nitrophenyl, anthryl, p-t-butoxyphenyl, or p-t-butycarboxyphenyl). Preferably, $R^6$ is substituted or unsubstituted alkyl or aryl as described above. When the detectable species are phenalenone dyes, $R^6$ is preferably at least 3 carbon atoms. Most preferably, $R^6$ is p-t-butylcarboxyphenyl.

FRAG is a detectable species as defined above. The specific composition of FRAG can vary considerably depending upon the type of detectable species desired and upon the particular detection means employed. The detectable species can be a material which is directly detectable by a suitable means, as well as a material which can react with other substances, for example, analytes, enzymes or other reagents to provide a detectable species.

Particularly useful detectable species are chromogens and fluorogens. Examples of useful classes of chromogens are azo, azomethine, nitrophenol, indophenol, indoaniline and triarylmethane dyes, and others known in the art, with azo dyes being preferred. Examples of useful classes of fluorogens are coumarin, umbelliferone, phenalenones, benzphenalenones, substituted and unsubstituted 4-oxo-4H-benz-[d,e]anthracenes, fluorescein and rhodamine fluorescent dyes, and others known in the art. Phenalenone dyes are particularly useful.

Useful phosphorescent species include such phosphors as 2′, 5′-dibromofluorescein and 4′,5′-diiodofluorescein. A useful chemiluminescent species is luciferin.

FRAG is linked to Q by means of a single bond through a bivalent monoatom linkage which is a part of FRAG. Preferably, the monoatom linkage is oxy, thio or seleno. However, when FRAG is fluorogen, the linkage is oxy or thio. Most preferably, Q is oxy.

$R^2$, $R^3$ and $R^4$ in the above quinone structure are independently hydrogen, substituted or unsubstituted alkyl of 1 to 40 carbon atoms (for example, methyl, ethyl, hydroxymethyl, methoxymethyl or benzyl) substituted or unsubstituted aryl (for example, phenyl, naphthyl, methylnaphthyl, p-nitrophenyl, m-methoxyphenyl, phenylsulfonamido or p-carboxyphenyl) or an electron withdrawing group which generally has a positive Hammett sigma value, and preferably has a sigma value greater than about 0.06. Hammett sigma values are calculated in accordance with standard procedures described, for example, in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (for example, fluoro, bromo, chloro or iodo), trihalomethyl (for example, trifluoromethyl or trichloromethyl), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species molecules to original RIND compound molecules.

At least one or $R^2$, $R^3$ and $R^4$, as defined above, must be an electron withdrawing group. Alternatively, $R^3$ and $R^4$, taken together, can represent the carbon atoms necessary to complete a substituted or unsubstituted fused strained carbocyclic ring attached to the quinone nucleus. For example, such a ring (mono- or bicyclic) can have from 4 to 8, and preferably from 5 to 7, carbon atoms in the backbone.

Representative RIND compounds are listed in Table I below in reference to the following structure:

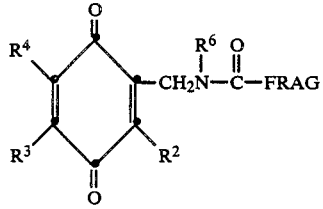

The $E_{\frac{1}{2}}$ values in Table I were determined for the quinone nucleus of this structure having a hydrogen atom in place of

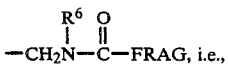

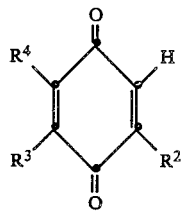

The $E_{\frac{1}{2}}$ values (where available) were measured in an aqueous emulsion of the quinone dissolved in N,N-dimethylformamide, a nonionic surfactant (TRITON X-100) and sodium phosphate buffer (pH 7). A standard calomel electrode was used as a standard. The $E_{\frac{1}{2}}$ values were corrected to a normal hydrogen electrode. Some $E_{\frac{1}{2}}$ values (denoted by *) were measured in acetonitrile using a saturated calomel electrode as a standard. $E_{\frac{1}{2}}$ values not available are denoted by "NA".

TABLE I
| RIND Compound | R⁶ | R² | R⁴ | R³ | FRAG | $E_{\frac{1}{2}}$ (mV) |
|---|---|---|---|---|---|---|
| I. | —CH₃ |  | same as R² |  |  | −528* |
| II. | —CH₃ | 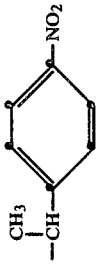 | same as R² | " | " | +236 |
| III. | —CH₃ | 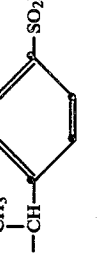 | same as R² | " | " | NA |
| IV. | —CH₃ |  | same as R² | " | " | −460* |
| V. | —CH₃ | 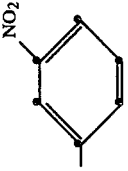 | R³ and R⁴ together form 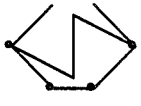 | | " | +214 |
| VI. | —CH₃ | 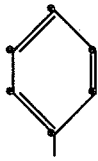 | | " | " | +180 |

TABLE I-continued

| RIND Compound | R⁶ | R² | R⁴ | R³ | FRAG | E₁ (mV) |
|---|---|---|---|---|---|---|
| VII. | —CH₃ | 4-NO₂-phenyl | | " | " | +236 |
| VIII. | —CH₃ | 4-SO₂NHCH(CH₃)₂-phenyl | | " | " | +212 |
| IX. | —CH₃ | 4-CN-phenyl | | " | " | +220 |
| X. | —CH₃ | 2-OCH₃-phenyl | | " | " | +154 |
| XI. | —CH₃ | 3,5-(NO₂)₂-phenyl | | " | " | +186 |
| XII. | —CH₃ | 4-COC₁₀H₂₁-phenyl | | " | " | +206 |
| XIII. | —CH₃ | 4-COCH₃-phenyl | | " | " | +212 |

TABLE I-continued

| RIND Compound | R⁶ | R² | R⁴ | R³ | FRAG | E½ (mV) |
|---|---|---|---|---|---|---|
| XIV. | —CH₃ | (4-Br-phenyl) | | | " | +192 |
| XV. | —CH₃ | —H | | | " | +213 |
| XVI. | —C₁₂H₂₅ | (4-CN-phenyl) | | | " | +220 |
| XVII. | —CH₃ | " | R⁴ and R³ together form (cyclic) | | " | +240 |
| XVIII. | —CH₃ | (4-NO₂-phenyl) | —t-butyl | —H | " | NA |
| XIX. | —CH₃ | (phenyl) | R⁴ and R³ together form (cyclic) | | " | +242 |
| XX. | —CH₃ | " | R⁴ and R³ together form (cyclic) | | " | +222 |

TABLE I-continued

| RIND Compound | R⁶ | R² | R⁴ | R³ | FRAG | E₁ (mV) |
|---|---|---|---|---|---|---|
| XXI. | —CH₃ | CH₃—CH—(C₆H₄)—SO₂NHC₁₀H₂₁ | same as R² | —CH₂N(CH₃)—C(=O)—FRAG | [naphthyl-azo-phenyl-SO₂NH₂ with OCH₃ and NHSO₂CH₃] | −528* |
| XXII. | —CH₃ | " | " | " | [methyl-phenyl-acrylate with OCH₃] | −528* |
| XXIII. | —CH₃ | [nitrophenyl] | R³ and R⁴ together form [cyclic] | | " | +214 |
| XXIV. | —CH₃ | [dichlorophenyl] | R³ and R⁴ together form [cyclic] | | [naphthyl-azo-phenyl(SO₂CH₃)(NO₂) with ONHSO₂-phenyl-SO₂NH₂] | +236 |
| XXV. | —CH₃ | —phenyl | R³ and R⁴ together form C₁₂H₂₅ | | " | +222 |

TABLE I-continued

| RIND Compound | R⁶ | R² | R⁴ | R³ | FRAG | E₁ (mV) |
|---|---|---|---|---|---|---|
| XXVI. | —CH₃ | " | —CH₃ | —CH₃ | " | +144 |
| XXVII. | —CH₃ | " | R³ and R⁴ together form (CH₃-cyclohexyl ring) | | " | +122 |
| XXVIII. | —CH₃ | " | R³ and R⁴ together form (CH₃)₂HC—CH₃ (isopropyl-methyl bicyclic) | | " | +174 |
| XXIX. | —CH₃ | 4-CN-phenyl | R³ and R⁴ together form (cyclopentyl ring) | | " | +220 |
| XXX. | —CH₃ | phenyl | R³ and R⁴ together form (cyclobutyl ring) | | " | +222 |
| XXXI. | —CH₃ | 2,4-dichlorophenyl | R³ and R⁴ together form | | " | +236 |

FRAG for XXIX (shown): methoxy-substituted phenalenone structure

TABLE I-continued

| RIND Compound | R⁶ | R² | R⁴ | R³ | FRAG | E₁ (mV) |
|---|---|---|---|---|---|---|
| XXXII. | —CH₃ | (4-NO₂-phenyl) | R³ and R⁴ together form | | " | +214 |
| XXXIII. | —CH₃ | (4-NO₂-phenyl) | " | | " | +236 |
| XXXIV. | —CH₃ | (4-SO₂NH(CH₃)₂-phenyl) | " | | " | +212 |
| XXXV. | —CH₃ | (4-COOH-phenyl) | " | | " | +220 |

RIND compounds XXIX, XXXI and XXXV are preferred in the practice of this invention.

The RIND compounds useful in the practice of this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of a compound from which the FRAG moiety is derived with the carbamoyl chloride. The precursor to the FRAG moiety has a hydroxy, mercapto or selenyl groups which reacts with the carbamoyl chloride. Preparation of these compounds is described in more detail in copending and commonly assigned U.S. Ser. No. 824,766 filed Jan. 31, 1986 by Belly et al and entitled REDUCIBLE COMPOUNDS AND ANALYTICAL COMPOSITIONS, ELEMENTS AND METHODS UTILIZING SAME, and U.S. Ser. No. 868,855 filed May 30, 1986 by Mura et al (noted above).

Other RIND compounds useful in the practice of this invention include those having the appropriate $E_{\frac{1}{2}}$ values and the structure CAR—($R^1$)$_n$ wherein:

(1) CAR— is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$. $R^1$ is

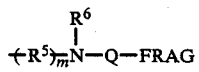

as defined above, and n is an integer of 1 or 2.

(2) CAR- is

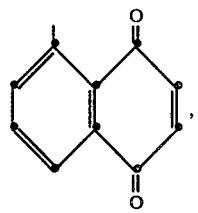

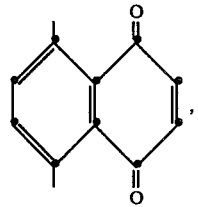

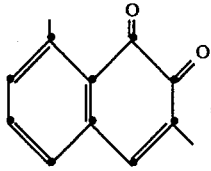

-continued

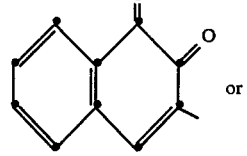

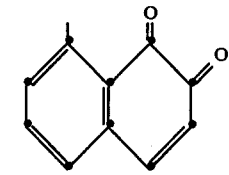

any of which can be substituted with one or more electron withdrawing groups as described above for $R^2$, $R^3$ and $R^4$. $R^1$ is

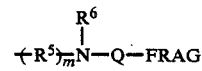

as defined above, and n is 1 or 2.

(3) CAR- is a substituted or unsubstituted nitrobenzenoid nucleus of the structure.

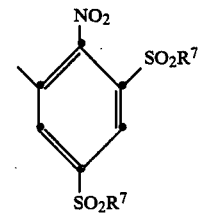

wherein $R^7$ is substituted or unsubstituted alkyl of 1 to 20 carbon atoms (for example, methyl, ethyl, methoxymethyl, isopropyl, dodecyl, hexadecyl or octadecyl), and $R^1$ is

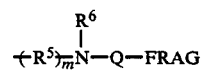

as defined above and n is 1. These compounds are similar to some described in U.S. Pat. No. 4,139,379 (noted above).

All of these reducible compounds can be prepared using techniques and starting materials known in the art or readily apparent to a skilled synthetic chemist.

Generally, the reducible compounds described herein have limited water solubility. Hence, it is best, when using them in an aqueous environment, to prepare a dispersion of the compound prior to use, for example, in a coating formulation. Such dispersions generally comprise the reducible compound, an aqueous buffer solution and either a solubilizing surfactant or a water-miscible organic solvent for the compound, or both. Surfactants which are useful in the practice of this invention include any surfactants which do not inhibit compound reduction. Nonionic surfactants are particularly useful.

Useful water-miscible organic solvents include alcohols (for example, methanol, ethanol or propanol), N,N- dimethylformamide, dimethyl sulfoxide, acetonitrile, hexamethylenephosphoramide and the like. The particular solvent to be used for a particular reducible compound can be readily determined by routine experimentation.

A dispersion can be prepared in the following general manner. The reducible compound is dissolved in the water-miscible solvent at a concentration which depends upon its molecular weight, but generally from about 1 to about 100, and preferably from about 5 to about 80, mg per ml of solvent. The resulting solution is then mixed with a suitable surfactant in an amount generally of from about 0.1 to about 24, and preferably from about 0.5 to about 10, ml surfactant per ml of dispersion. This preparation is generally carried out at room temperature.

These dispersions generally contain the organic buffer described above in an amount effective to maintain a physiological pH (9 or less) and to substantially eliminate the interference of dehydroascorbic acid as described above.

In one embodiment, the reducible compounds are water-compatible and compositions can be prepared using a suitable buffer of this invention and preferably a water-miscible solvent as described above.

The present invention is useful for determination of various biological or chemical substances in any fluid including wastewater, food stuffs, brewing, food and chemical manufacturing solutions and biological fluids. It is particularly useful in the determination of enzymes, substrates or living organisms (for example, microorganisms, yeast or white blood cells) in human or animal biological fluids, such as urine, serum, whole blood, sputum, spinal fluid, etc. Organisms commonly found in the human urinary tract are determined with this invention to advantage.

The assay of this invention is preferably carried out in the presence of an electron transfer agent (identified herein as an ETA), especially where the analyte is a living organism. The presence of an ETA provides more rapid dye release. It is a mobile compound which acts as an intermediary between the analyte and the reducible compound. They are generally present at a concentration that is dependant upon the concentration of the reducible compound, but preferably at a concentration of from about $1 \times 10^{-7}$ molar to about $1 \times 10^{-3}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds are those which are the subject of copending and commonly assigned U.S. Ser. No. 699,374 of Mura et al filed Feb. 7, 1985, now U.S. Pat. No. 4,746,607. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2-hydroxymethyl-1,4-naphthoquinone and 2-(2-hydroxyethyl)-1,4-naphthoquinone.

The determination of living cells is often carried out in the presence of a nutrient for those cells although its presence is not essential. Any nutrient media can be used which contains useful carbon, and optionally nitrogen, sources. Suitable nutrient media having proper components and pH are well known in the art.

In the present invention, the amount of the reducible compound used can be varied widely depending upon the particular compound used and the analyte to be determined, but it is generally present in an amount of at least about 0.001, and preferably from about 0.01 to about 1, millimolar.

The present invention is adaptable to either solution of dry assays. In a solution assay, a solution (or aqueous dispersion) containing a reducible compound, an organic buffer and preferably an ETA, can be prepared and contacted, by mixing, with a liquid test sample suspected of containing the analyte to be determined. Generally, the composition is mixed with the test sample in a suitable container (for example, test tube, petri dish, beaker, cuvette or test device). The resulting solution (or dispersion) is gently mixed and incubated for a relatively short time (that is, up to about 30 minutes) at a temperature up to about 50° C., and generally from about 20° to about 40° C. The test sample is then evaluated by measuring the detectable change resulting from reduction of the reducible compound by the analyte using suitable detection equipment.

A pretreatment step to remove additional interferents or to concentrate cells can also be carried out before the assay, if desired.

The solution assay can also be carried out by contacting a porous absorbent material, e.g. paper strip, containing a test sample with a dispersion of the reducible compound and an organic buffer. The analyte (for example, microorganisms) in the test sample can migrate from the porous material into the dispersion and initiate the analytical reactions needed for the assay.

Alternatively, the method of this invention can be practiced with a dry analytical element. Such an element can be a absorbent carrier material, i.e. a thin sheet or strip of self-supporting absorbent or bibulous material, such as filter paper or strips, which contains the reducible compound and organic buffer or a dried residue of same. Such elements are known in the art as test strips, diagnostic elements, dip sticks, diagnostic agents and the like.

When employed in dry analytical elements, the reducible compounds and organic buffers described herein can be incorporated into a suitable absorbent carrier material by imbibition or impregnation, or can be coated on a suitable absorbent carrier material. Useful carrier materials are insoluble and maintain their structural integrity when exposed to water or physiological fluids such as urine or serum. They can be prepared from paper, porous particulate structures, cellulose, porous polymeric films, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

In one embodiment, an analytical element comprises a nonporous support having thereon at least one porous spreading zone as the absorbent carrier material. The reducible compound or buffer can be in the spreading zone or in a different zone (for example, a reagent zone, registration zone or hydrophilic zone). The spreading zone can be prepared from any suitable fibrous or nonfibrous material or mixtures of either or both.

The spreading zone can be prepared using fibrous materials, either mixed with a suitable binder material or woven into a fabric, as described in U.S. Pat. No. 4,292,272 (issued Sept. 29, 1981 to Kitajima et al), from polymeric compositions or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese patent publication No. 57(1982)-101760 (published June 24, 1982). It is desired that the spreading zones be isotropically porous, meaning that the porosity is the same in each direction in the zone as created by interconnected spaces or pores between particles, fibers, polymeric strands, etc.

Suitable supports can be any suitable dimensionally stable, and preferably, transparent (that is, radiation transmissive) film or sheet material which transmits electromagnetic radiation of a wavelength between about 200 and about 900 nm. A support of choice for a particular element should be compatible with the intended mode of detection (for example, reflection, fluorescence or transmission spectroscopy) and inert to chemical reagents and liquid samples used in the assay. Useful support materials include polystyrene, polyesters, polycarbonates, cellulose esters and others known in the art.

The elements can have a multiplicity of zones which can be superposed layers or distinct areas in the same layer. The reducible compound, organic buffer and any other reagents can be located in the same or different zones within the element. It is preferred, however, that the organic buffer be "in association with" the reducible compound. This means that the buffer and compound are located relative to each other such that when the element is used in an assay, they quickly become mixed and interact with each other. Element configurations are well known in the art, as described, for example in the patents noted above.

A variety of different elements can be prepared in accordance with the present invention. Elements can be configured in a variety of forms, including elongated tapes of any desired width, sheets, slides or chips.

The method carried out with an element can be manual or automated. In general, differentiation is made by taking the element from a supply roll, chip packet or other source and contacting it with a sample (for example, up to 200 μl) of the liquid to be tested to that the sample mixes with the reagents in the element. Such contact can be accomplished in any suitable manner, for example, by dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result. Determination of an analyte is achieved when the reducible compound is reduced releasing a species which can be detected in a suitable manner. In some instances, the organic buffer and test sample may be mixed and pretreated (as described above for a solution assay) prior to applying the mixture to the element containing the reducible compound.

Materials used in the following examples were obtained as follows:

Trimethyl-1,4-benzoquinone (TMBQ) was prepared by a standard oxidation of the corresponding hydroquinone, which was obtained from Aldrich Chem. Co. (Milwaukee, Wisconsin, U.S.A.)

Dehydroascorbic acid (DHA) was prepared by a published procedure: M. Ohmori & M. Takagi, *Agricultural & Biological Chemistry*, 42(1), 173–174 (1978).

TRITON X-100 nonionic surfactant from Rohm and Haas (Philadelphia, Pennsylvania, U.S.A.), and buffers from either Sigma Chemical Co. (St. Louis, Missouri, U.S.A.) or from Eastman Kodak Company (Rochester, New York, U.S.A.). All other reagents were also obtained from Eastman Kodak Co. or prepared using readily available starting materials and standard procedures.

EXAMPLES 1–12: ANALYTICAL COMPOSITIONS

These examples illustrate several analytical compositions of this invention and their ability to reduce the interference by dehydroascorbic acid in an assay. A number of Control compositions outside of this invention are also illustrated and compared to the invention compositions.

The analytical compositions were each prepared with a dispersion of RIND IX from Table I above ($8 \times 10^{-5}$ molar), organic buffer (0.1 molar), and trimethyl-1,4-benzoquinone electron transfer agent ($1.7 \times 10^{-4}$ molar). The pH of each composition was about 7.5. Control compositions containing inorganic buffers outside the scope of this invention were similarly prepared.

Dehydroascorbic acid (1.15 millimolar) was added to each composition, and the amount of dye from the reducible compound was measured at 635 nm using a standard spectrophotometer after incubation at 37° C. for 30 minutes. Because dehydroascorbic acid is the only reductant in the test, the amount of dye released is a measure of the amount of interference by the acid. A low amount of released dye corresponds to low interference. The buffers differ in their capacity to reduce the interference by dehydroascorbic acid. The results are shown in Table II below wherein the optical density is a measure of the dye released. An optical density of about 0.9 or less indicates reduced interference, whereas a density of less than about 0.4 is preferred.

TABLE II

| Test | Buffer | Optical Density |
|---|---|---|
| Control A | Sodium phosphate (0.125 molar) | 1.3 |
| Control B | Sodium cacodylate | 1.9 |
| Example 1 | N—tris(Hydroxymethyl)methyl-2-aminoethanesulfonic acid | 0.03 |
| Example 2 | Triethylamine | 0.22 |
| Example 3 | N—2-Hydroxyethylpiperazine-N'—2-ethanesulfonic acid | 0.39 |
| Example 4 | 3-(N—Morpholino)propanesulfonic acid | 0.40 |
| Example 5 | Tris(hydroxymethyl)aminomethane | 0.04 |
| Example 6 | Bis(2-hydroxyethyl)imino-tris(hydroxymethyl)methane | 0.098 |
| Example 7 | N,N—bis(2-Hydroxyethyl)-2-aminoethane sulfonic acid | 0.109 |
| Example 8 | N,N—bis(2-Hydroxyethyl)glycine | 0.134 |
| Example 9 | N—tris(Hydroxymethyl)methylglycine | 0.344 |
| Example 10 | Imidazole | 0.44 |

TABLE II-continued

| Test | Buffer | Optical Density |
|---|---|---|
| Example 11 | N,N—Dimethylglutaric acid | 0.71 |
| Example 12 | N—(2-Acetamido)-2-aminoethanesulfonic acid | 0.85 |

EXAMPLES 13 AND 14: COMPARATIVE SOLUTION ASSAY FOR ESCHERICHIA COLI (E. COLI)

This assay demonstrates the use of the present invention to determine *E. coli* microorganisms and provides a comparison to an assay of the prior art. It also compares this invention to a similar assay using borate as the buffer.

A dispersion of RIND IX (from Table I) was prepared by dissolving RIND IX (2 mg) in N,N-dimethylformamide (DMF, 125 μl) containing 0.1% sulfuric acid, and adding TRITON X-100 nonionic surfactant (250 μl) and 12.5 ml of the appropriate buffer (TES for Example 13, triethylamine for Example 14 and sodium borate for the Control). *E. coli* cells were grown in brain heart infusion media (Difco Labs, Detroit, Michigan, U.S.A.) at 37° C. overnight without shaking. The cells (40 ml) were harvested by centrifugation, washed with and resuspended in the appropriate buffer.

Test solutions were prepared from the following:

RIND IX dispersion from about (1500 μl), final concentration of $8 \times 10^{-5}$ molar, trimethyl-1,4-benzoquinone electron transfer agent solution (25 μl of 3 mg/ml of methanol), final concentration of $1.7 \times 10^{-4}$ molar, glucose solution (60 μl of 100 mg/ml water), final concentration of $1.1 \times 10^{-2}$ molar,

*E. coli* cells from above (20 ml), final concentration of about $2.4 \times 10^6$ cells/ml, and the appropriate buffer (750 ml), final concentration of 0.1 molar.

Solutions containing no cells were also prepared to measure background. The optical densities (OD) of all solutions were measured at 635 nm right after they were mixed and after 30 minutes at 37° C. Table III below shows the results of the measurements in terms of the change in optical density after 30 minutes (ΔOD) for both test solutions and background solutions. It is clear that using the borate buffer in the Control reduces the sensitivity of the assay.

TABLE III

| | Δ OD After 30 Minutes at 635 nm | |
|---|---|---|
| Buffer | Test Solution | Background Solution |
| Example 13 (TES) | 1.59 | 0.17 |
| Example 14 (Triethylamine) | 1.56 | 0.03 |
| Control (Borate) | 0.80 | 0.057 |

EXAMPLE 15: COMPARATIVE DRY ASSAY

This example compares the present invention practiced with a dry analytical element of this invention to a dry assay carried out with phosphate buffer.

Stock solutions were prepared as follows:

(1) dehydroascorbic acid (DHA), 20 mg/ml of water, (2) RIND IX dispersion: 2 mg RIND compound in 125 μl DMF and 250 μl TRITON X-100 nonionic surfactant, then 37.5 μl portions of this solution were individually added to 1 ml of 50 millimolar TES buffer (pH 7.5) and 1 ml of 50 ml sodium phosphate buffer (pH 7.5), and (3) TMBQ electron transfer agent, 3 mg/ml methanol.

Test solutions were prepared by adding 20 μl of solution (3) to 1 ml of RIND solution (2) in TES and phosphate buffers. Samples of these solutions (50 μl) were spotted onto a paper element (Beckman Blotters, Beckman Instruments, Inc., Fullerton, California, U.S.A.): the TES solution on one side of the element and the phosphate solution on the other side. The paper was then allowed to dry at 25° C. for 30 minutes. DHA solution (1)(10 μl) was then spotted onto the areas of the element contacted by the the buffer solutions.

The area of the element contacted by the RIND compound and the phosphate buffer turned blue, indicating that the DHA prematurely reduced the RIND compound, releasing dye. The area of the element contacted with the RIND compound and TES buffer did not show any color change, indicating no premature reduction of the RIND compound by DHA in the presence of TES.

The invention has been described in detail with particular reference to preferred embodiments thereof, but it will be understood that variations and modifications can be effected within the spirit and scope of the invention.

We claim:

1. An aqueous analytical composition for the determination of an analyte comprising:
(a) a dye or dye-providing compound capable of being reduced to provide a detectable species by an analyte and dehydroascorbic acid, and
(b) a nitrogen-containing organic buffer which buffers said composition at physiological pH,
said dye or dye-providing compound represented by the structure CAR-(-R¹)ₙ wherein CAR- is a carbocyclic aromatic or quinone nucleus, R¹ is

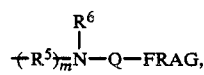

wherein R⁵ is alkylene of 1 or 2 carbon atoms, R⁶ is alkyl, cycloalkyl or carbocyclic aryl, Q is carbonyl or thiocarbonyl, FRAG is a moiety which provides a detectable chromogen or fluorogen when released from said reducible dye or dye-providing compound upon reduction by said analyte or dehydroascorbic acid, m is 0 or 1, and n is 1 or 2, provided said reducible dye or dye-providing compound is capable of being reduced at physiological pH to release said chromogen or fluorogen, and further provided that when R¹ is replaced with H, CAR-(-H)ₙ has an $E_{\frac{1}{2}}$ of either at least about +100 mV when measured in water, or of at least about −650 mV when measured in acetonitrile.

2. The composition of claim 1 further comprising an electron transfer agent and a nutrient for living cells containing useful carbon.

3. The composition of claim 1 wherein said organic buffer is selected from the group consisting of:
N-tris(Hydroxymethyl)methyl-2-aminoethanesulfonic acid,
Triethylamine,
N-2-Hydroxyethylpiperazine-N'-2-ethanesulfonic acid,
3-(N-Morpholino)propanesulfonic acid, Tris(hydroxymethyl)aminomethane,
Bis(2-hydroxyethyl)iminotris(hydroxymethyl)methane,
N,N-bis(2-Hydroxyethyl)-2-aminoethanesulfonic acid,
N,N-bis(2-Hydroxyethyl)glycine,
N-tris(Hydroxymethyl)methylglycine,
Imidazole,
N,N-Dimethylglutaric acid,
N-(2-Acetamido)-2-aminoethanesulfonic acid,
N-Ethylmorpholine,
Diethanolamine,
2-Amino-2-methyl-1,3-propanol,
Trimethylpyridines, and
Barbituric acid.

4. The composition of claim 3 wherein said organic buffer is N-tris(hydroxymethyl)methyl-2-aminoethanesulfonic acid or tris(hydroxymethyl)-aminomethane.

5. The composition of claim 1 buffered to a pH in the range of from about 6.5 to about 8.5.

6. The composition of claim 1 wherein said organic buffer is present in an amount of at least about 0.005 millimolar.

7. The composition of claim 1 wherein CAR- is

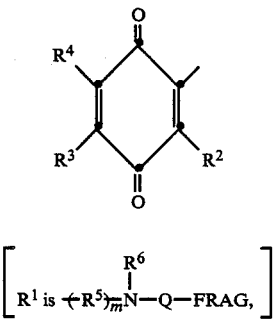

$$\left[ R^1 \text{ is } \left( R^5 \right)_{\overline{m}} \overset{R^6}{\underset{|}{N}} - Q - \text{FRAG,} \right]$$

$R^2$ and $R^4$ are independently hydrogen, alkyl, carbocyclic aryl or an electron withdrawing group having a positive Hammett sigma value, and $R^3$ is $R^1$, hydrogen, alkyl, carbocyclic aryl or an electron withdrawing group having a positive Hammett sigma value, provided at least one of $R^2$, $R^3$ and $R^4$ is an electron withdrawing group having a positive Hammett sigma value of $R^3$ and $R^4$, taken together, represent the atoms necessary to complete a nonaromatic strained, fused carbocyclic 4- to 8-membered ring.

8. An analytical element for the determination of an analyte comprising an absorbent carrier material and containing:
(a) a dye or dye-providing compound capable of being reduced to provide a detectable species by an analyte and dehydroascorbic acid, and
(b) a nitrogen-containing organic buffer which buffers said composition at physiological pH,
said dye or dye-providing compound represented by the structure $\text{CAR}-(R^1)_n$ wherein CAR- is a carbocyclic aromatic or quinone nucleus, $R^1$ is

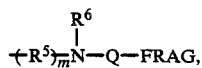

wherein $R^5$ is alkylene of 1 or 2 carbon atoms, $R^6$ is alkyl, cycloalkyl or carbocyclic aryl, Q is carbonyl or thiocarbonyl. FRAG is a moiety which provides a detectable chromogen or fluorogen when released from said reducible dye or dye-providing compound upon reduction by said analyte or dehydroascorbic acid, m is 0 or 1, and n is 1 or 2, provided said reducible dye or dye-providing compound is capable of being reduced at physiological pH to release said chromogen or fluorogen, and further provided that when $R^1$ is replaced with H, CA-R-(H)$_n$ has an $E_{\frac{1}{2}}$ of either at least about $+100$ mV when measured in water, or of at least about $-650$ mV when measured in acetonitrile.

9. The element of claim 8 further comprising an electron transfer agent and a nutrient for living cells containing useful carbon.

10. The element of claim 8 wherein said buffer is selected from the group consisting essentially of:
N-tris(Hydroxymethyl)methyl-2-aminoethanesulfonic acid,
Triethylamine,
N-2-Hydroxyethylpiperazine-N'-2-ethanesulfonic acid,
3-(N-Morpholino)propanesulfonic acid,
Tris(hydroxymethyl)aminomethane,
Bis(2-hydroxyethyl)iminotris(hydroxymethyl)methane,
N,N-bis(2-Hydroxyethyl)-2-aminoethanesulfonic acid,
N,N-bis(2-Hydroxyethyl)glycine,
N-tris(Hydroxymethyl)methylglycine,
Imidazole,
N,N-Dimethylglutaric acid,
N-(2-Acetamido)-2-aminoethanesulfonic acid,
N-Ethylmorpholine,
Diethanolamine,
2-Amino-2-methyl-1,3-propanol,
Trimethylpyridines, and
Barbituric acid.

11. The element of claim 8 wherein CAR- is

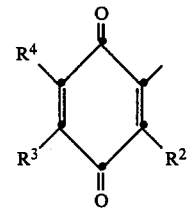

$$\left[ R^1 \text{ is } \left( R^5 \right)_{\overline{m}} \overset{R^6}{\underset{|}{N}} - Q - \text{FRAG,} \right]$$

$R^2$ and $R^4$ are independently hydrogen, alkyl, carbocyclic aryl or an electron withdrawing group having a positive Hammett sigma value, and $R^3$ and $R^1$, hydrogen, alkyl, carbocyclic aryl or an electron withdrawing group having a positive Hammett sigma value, provided at least one or $R^2$, $R^3$ and $R^4$ is an electron withdrawing group having a positive Hammett sigma value or $R^3$ and $R^4$, taken together, represent the atoms necessary to complete a nonaromatic, strained, fused carbocyclic 4- to 8-membered ring.

12. A method for the reduction of interference by dehydroascorbic acid in a determination of an analyte which is substantially unaffected by the presence of dehydroascorbic acid comprising the steps of:
A. contacting a sample of a liquid suspected of containing an analyte and dehydroascorbic acid with (a) a dye or dye-providing compound capable of being reduced to provide a detectable species by said analyte and dehydroascorbic acid, and (b) a nitrogen-containing organic buffer which buffers said liquid sample at physiological pH, and B. determining said detectable species resulting from the presence of said analyte, said dye or dye-providing compound represented by the structure CAR—R$^1$)$_n$ wherein CAR- is a carbocyclic aromatic or quinone nucleus, R$^1$ is

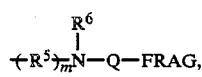

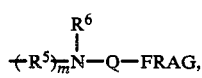

wherein R$^5$ is alkylene of 1 or 2 carbon atoms, R$^6$ is alkyl, cycloalkyl or carbocyclic aryl, Q is carbonyl or thiocarbonyl. FRAG is a moiety which provides a detectable chromogen or fluorogen when released from said reducible dye or dye-providing compound upon reduction by said analyte or dehydroascorbic acid, m is 0 or 1, and n is 1 or 2, provided said reducible dye or dye-providing compound is capable of being reduced at physiological pH to release said chromogen or fluorogen, and further provided that when R$^1$ is replaced with H, CAR—(H)$_n$ has an E$_{\frac{1}{2}}$ of either at least about +100 mV when measured in water, or of at least about −650 mV when measured in acetonitrile.

13. The method of claim 12 carried out in the presence of an electron transfer agent and a nutrient for living cells containing useful carbon.

14. The method of claim 12 wherein said organic buffer is selected from the group consisting essentially of:
N-tris(Hydroxymethyl)methyl-2-aminoethanesulfonic acid,
Triethylamine,
N-2-Hydroxyethylpiperazine-N'-2-ethanesulfonic acid,
3-(N-Morpholino)propanesulfonic acid,
Tris(hydroxymethyl)aminomethane,
Bis(2-hydroxyethyl)iminotris(hydroxymethyl)methane,
N,N-bis(2-Hydroxyethyl)-2-aminoethanesulfonic acid,
N,N-bis(2-Hydroxyethyl)glycine,
N-tris(Hydroxymethyl)methylglycine,
Imidazole,
N,N-Dimethylglutaric acid,
N-(2-Acetamido)-2-aminoethanesulfonic acid,
N-Ethylmorpholine,
Diethanolamine,
2-Amino-2-methyl-1,3-propanol,
Trimethylpyridines, and
Barbituric acid.

15. The method of claim 14 wherein said organic buffer is N-tris(hydroxymethyl)methyl-2-aminoethanesulfonic acid or tris(hydroxymethyl)aminomethane.

16. The method of claim 12 carried out at a pH in the range of from about 6.5 to about 8.5.

17. The method of claim 12 for the determination of microorganisms.

18. The method of claim 17 for the determination of microorganisms in urine.

* * * * *

UNITED STATES PATENT AND TRADEMARK OFFICE
CERTIFICATE OF CORRECTION

PATENT NO. : 4,885,240

DATED : 5 December 1989

INVENTOR(S) : Annie L. Wu

It is certified that error appears in the above-identified patent and that said Letters Patent is hereby corrected as shown below:

Column 29, line 35, delete formula " $\left[ R^1 \text{ is } \left( R^5 \right)_{\overline{m}} \underset{|}{\overset{R^6}{N}} - Q - FRAG. \right]$ "; 
line 44, delete "of" and insert - -or- -.

Column 30, line 48, delete formula " $\left[ R^1 \text{ is } \left( R^5 \right)_{\overline{m}} \underset{|}{\overset{R^6}{N}} - Q - FRAG. \right]$ ".

Column 31, line 20, delete formula " $\left( R^5 \right)_{\overline{m}} \underset{|}{\overset{R^6}{N}} - Q - FRAG.$ " which incorrectly appears twice.

Signed and Sealed this

Thirty-first Day of March, 1992

Attest:

HARRY F. MANBECK, JR.

*Attesting Officer*   *Commissioner of Patents and Trademarks*